(12) United States Patent
McNair

(10) Patent No.: US 12,367,981 B2
(45) Date of Patent: *Jul. 22, 2025

(54) CLASSIFIER APPARATUS WITH DECISION SUPPORT TOOL

(71) Applicant: Cerner Innovation, Inc., Kansas City, MO (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 120 days.

This patent is subject to a terminal disclaimer.

(21) Appl. No.: 18/364,554

(22) Filed: Aug. 3, 2023

(65) Prior Publication Data

US 2023/0377750 A1 Nov. 23, 2023

Related U.S. Application Data

(63) Continuation of application No. 16/595,073, filed on Oct. 7, 2019, now Pat. No. 11,769,592.
(Continued)

(51) Int. Cl.
*G16H 50/20* (2018.01)
*A61B 5/0205* (2006.01)
(Continued)

(52) U.S. Cl.
CPC ........... *G16H 50/20* (2018.01); *A61B 5/0205* (2013.01); *C07K 16/36* (2013.01);
(Continued)

(58) Field of Classification Search
CPC ...... G16H 50/20; A61B 5/0205; C07K 16/36; C07K 16/44; G06F 18/2413; G16B 20/20; A61M 25/00
See application file for complete search history.

(56) References Cited

U.S. PATENT DOCUMENTS

| 9,922,285 B1 | 3/2018 | Glode et al. |
| 2014/0056889 A1 | 2/2014 | Morimoto et al. |

(Continued)

OTHER PUBLICATIONS

Crous-Bou, Marta, et al. "Interactions of established risk factors and a GWAS-based genetic risk score on the risk of venous thromboembolism." Thrombosis and haemostasis 116.10 (2016): 705-713. (Year: 2016).*

(Continued)

*Primary Examiner* — Olivia M. Wise
*Assistant Examiner* — Mary C Leverett
(74) *Attorney, Agent, or Firm* — Invoke

(57) ABSTRACT

Technologies are provided for an improved classifier apparatus and processes for improving the accuracy of classification technology including example applications of such classifiers. A process includes applying clustering to variables contributing to the classification task. The clusters may be represented in a 1-dimensional, 2-dimensional, or 3-dimensional matrix that is a spatial abstraction of the interrelationships. A convolutional transformation may be applied to the matrix so as to reduce the effective dimensionality of the classification problem and improve the signal-to-noise ration. A deep learning neural network method may be applied to the transformed network to generate an improved classification model, which may be utilized by a decision support tool. One embodiment comprises a decision support tool for detecting risk of venous thrombosis and venous thromboembolism (VTE) in a patient, based on phenotype and genomics information.

23 Claims, 13 Drawing Sheets

Related U.S. Application Data

(60) Provisional application No. 62/742,362, filed on Oct. 7, 2018.

(51) Int. Cl.
*A61M 25/00* (2006.01)
*C07K 16/36* (2006.01)
*C07K 16/44* (2006.01)
*G06F 18/2413* (2023.01)
*G16B 20/20* (2019.01)

(52) U.S. Cl.
CPC ......... *G06F 18/2413* (2023.01); *G16B 20/20* (2019.02); *A61M 25/00* (2013.01); *C07K 16/44* (2013.01); *C07K 2317/60* (2013.01)

(56) References Cited

U.S. PATENT DOCUMENTS

| | | |
|---|---|---|
| 2017/0027498 A1 | 2/2017 | Larson et al. |
| 2018/0039732 A1 | 2/2018 | Szeto et al. |
| 2019/0355438 A1 | 11/2019 | Venn et al. |

OTHER PUBLICATIONS

Agharezaei, Laleh, et al. "The prediction of the risk level of pulmonary embolism and deep vein thrombosis through artificial neural network." Acta Informatica Medica 24.5 (2016): 354. (Year: 2016).*

Heit, John A., et al. "A genome-wide association study of venous thromboembolism identifies risk variants in chromosomes 1q24. 2 and 9q." Journal of thrombosis and haemostasis 10.8 (2012): 1521-1531. (Year: 2012).*

Kelley, David R. et al.; "Basset: learning the regulatory code of the accessible genome with deep convolutional neural networks"; 2016' Cold Spring Harbor Laboratory Press; pp. 990-999. (Year: 2016).

Ionita-Laza I, Lee S, Makarov V, Buxbaum JD, Lin X. Sequence kernel association tests for the combined effect of rare and common variants. Am J Hum Genet. Jun. 6, 2013;92(6):841-53. (Year: 2013).

Penco, S. etal.; "Assessment of the Role of Genetic Polymorphism in Venous Thrombosis Through Artificial Neural Networks"; 2005; University College London; Annals of Human Genetics 69; pp. 693-706. (Year: 2005).

Pre interview First Office Action received for U.S. Appl. No. 16/596,227, mailed on Aug. 4, 2022, 4 pages.

* cited by examiner

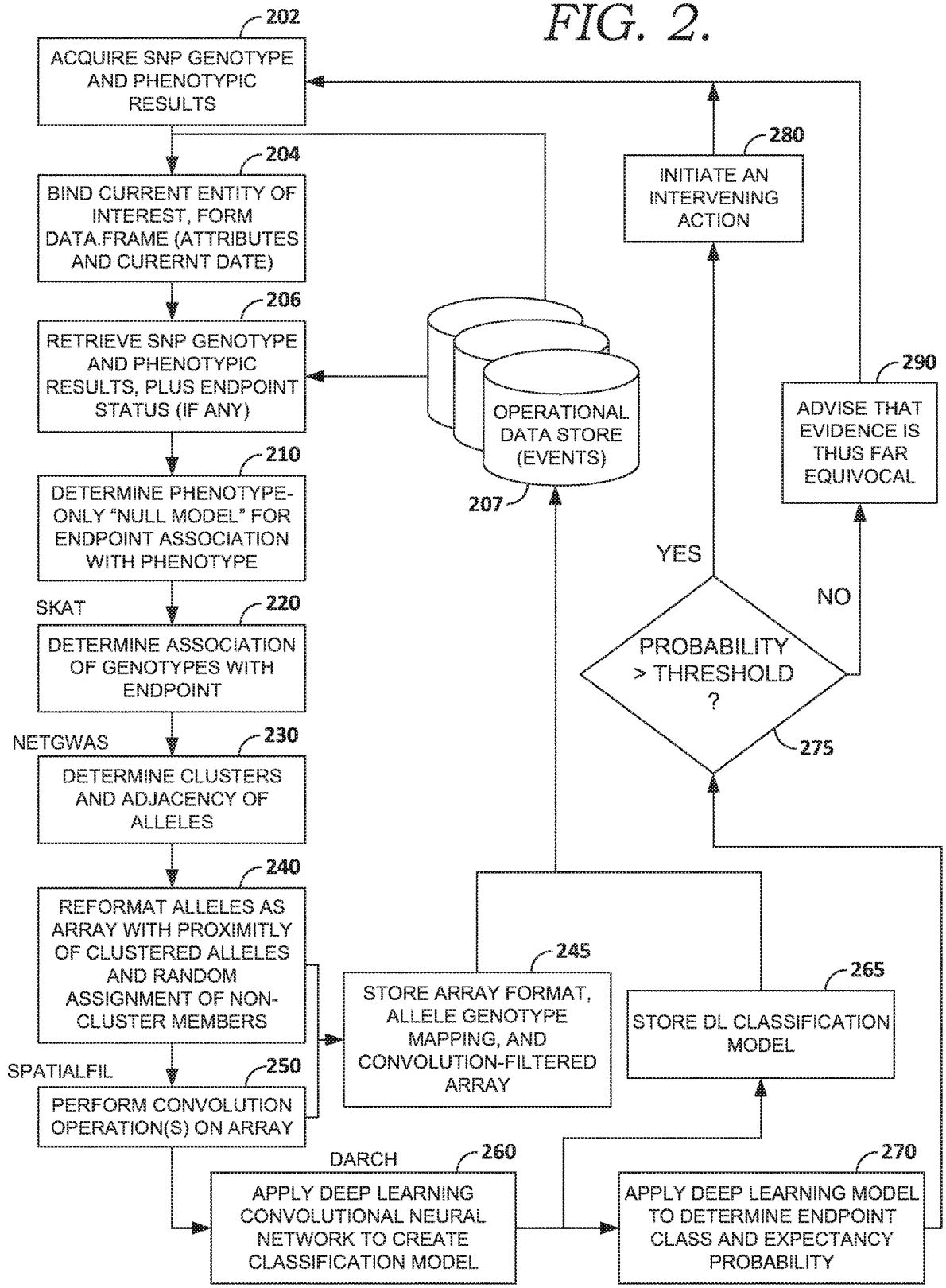

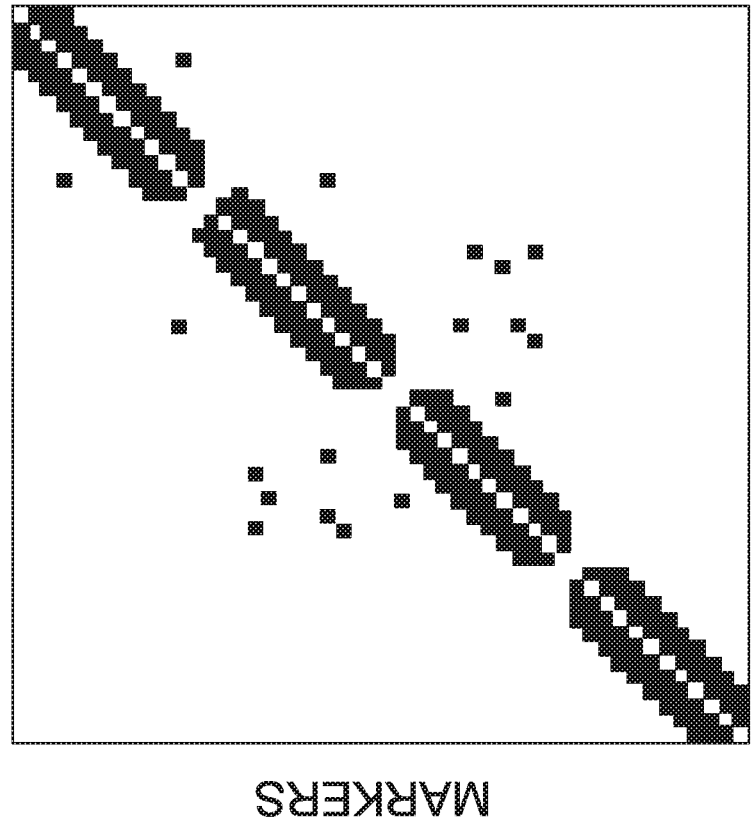
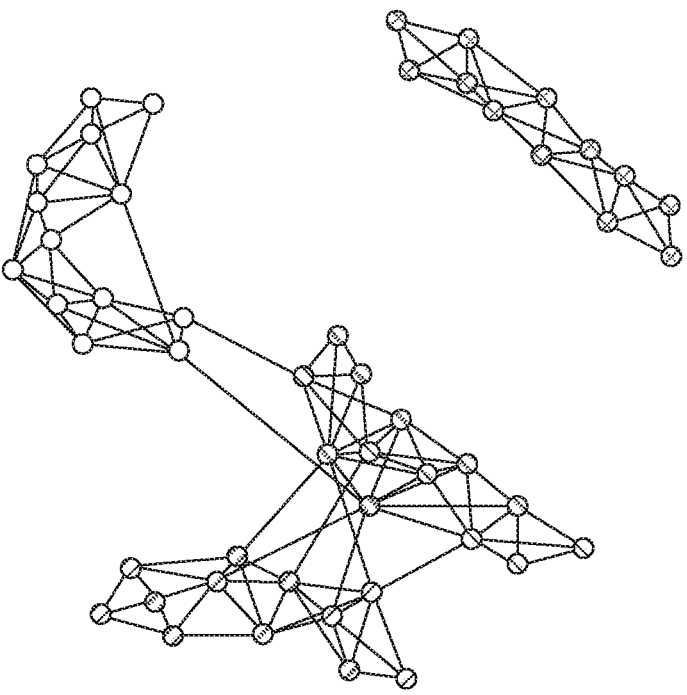
FIG. 4A.

| ITEM | VALUE |
|---|---|
| SENSITIVITY | 99% |
| SPECIFICITY | 95% |
| EVENT PREVALENCE | 50% |
| POSITIVE PREDICTIVE VALUE (PPV) | 95% |
| NEGATIVE PREDICTIVE VALUE (NPV) | 99% |

*FIG. 6.*

```
###########################################################################

#   VTE Sequence Kernel Association - Example

###########################################################################
library(SKAT)
# load data 2,000 subjects (1,000 persons with materialized VTE; 1,000 age-gender matched persons without VTE)
# Padua scores dichotomized (<=3 ; >3)
dat1 <- read.csv(file="c:/0_cerdsm/IP/VTE/X.csv", header=TRUE,
        colClasses="numeric")
len.X <- length(dat1[[1]])
colnam <- colnames(dat1)
len.col <- length(colnam)
X <- rep(0, len.X)
for (i in 1:len.X) {
  X[i] <- dat1[i,1]
} genotypes at 30 SNPs
dat2 <- read.csv(file="c:/0_cerdsm/IP/VTE/Z.csv", header=TRUE,
        colClasses=rep("numeric",30))
len.Z <- length(dat2[[1]])
colnam <- colnames(dat2)
len.col <- length(colnam)
Z <- matrix(rep(0, len.Z*len.col), ncol=len.col)
for (i in 1:len.col) {
  Z[,i] <- dat2[[i]]
} outcomes (VTE=1, no_VTE=0)
dat3 <- read.csv(file="c:/0_cerdsm/IP/VTE/y.csv", header=TRUE,
        colClasses="numeric")
len.y <- length(dat3[[1]])
colnam <- colnames(dat3)
y <- rep(0, len.y)
for (i in 1:len.y) {
  y[i] <- dat3[i,1]
} calculate NULL model for dichotomized Padua score in X, to determine likelihood of VTE in the absence of any
genomics information
obj <- SKAT_Null_Model(y ~ X, out_type="D")

# determine statistical association of genotypes in Z with VTE outcome
# use logistic weighting to allocate greater evidentiary strength to SNPs having low minor-allele frequencies (< 4%) in
# the population
wt <- Get_Logistic_Weights(Z, par1=0.02, par2=200)
SKAT(Z, obj, impute.method="bestguess", max_maf=0.15, missing_cutoff=0.10, method="davies",
kernel="linear.weighted", weights=wt)$p.value
[1] 0.00433 test for joint presence of common and rare SNPs
SKAT_CommonRare(Z, obj, r.corr.rare=1, r.corr.common=1, method="A")$p.value
[1] 0.01753 conclude that these 30 SNP polymorphisms are highly significant statistically to development of VTE
```

FIG. 7.

```
###########################################################################

#   Determine intra- and inter-chromosome SNP genotype correlations-based adjacency

##################################################################### library(Matrix)
library(igraph)
library(netgwas)

# genotypes at 30 SNPs
dat2 <- read.csv(file="c:/0_cerdsm/IP/VTE/Z.csv", header=TRUE,
         colClasses=rep("numeric",30))
len.Z <- length(dat2[[1]])
colnam <- colnames(dat2)
len.col <- length(colnam)
Z <- matrix(rep(0, len.Z*len.col), ncol=len.col)
for (i in 1:len.col) {
  Z[,i] <- dat2[[i]]
} determine adjacency matrix
set.seed(1239)
out <- netsnp(data=Z, n.rho=4, method="gibbs", ncores="all")

plot(out)
str(out)
out$path[[4]]  # adjacency
image(out$path[[4]])
# package igraph also provides conversions from and to sparse matrices (of package Matrix) via its
graph.adjacency() and get.adjacency().

# coerce to non-sparse matrix object
out2 <- as.matrix(out$path[[4]])

# two clusters of SNPs exhibiting adjacency-type correlations
A = {6,20,24},  B = {14,23,28} define square array to contain assignments of SNPs based on adjacency
assign non-adjacent SNPs randomly
patch.nbr <- round(sqrt(len.col),0) + 1
patch.siz <- 5 # odd, so that each patch has a central cell surrounded on each side by 2 cells
SNP.array <- matrix(rep(0, (patch.nbr*patch.siz)^2), nrow=patch.nbr*patch.siz)
x.cells <- seq(from=3, to=patch.nbr*patch.siz, by=5)
y.cells <- seq(from=3, to=patch.nbr*patch.siz, by=5)
avail.patch.centers <- matrix(rep(1, length(x.cells)*length(y.cells)), nrow=length(x.cells))

# retrieve SNP clusters of SNPs having adjacency
clus <- data.frame(cl1=c(6,20,24), cl2=c(14,23,28))
len.clus <- length(clus)

# identify SNPs lacking adjacency
snps <- seq(1:len.col)
nonadj.snps <- snps[-unlist(clus)]
len.nonadj <- length(nonadj.snps)
```

⋮

CONTINUES IN FIG. 8B

FIG. 8A.

CONTINUES FROM FIG. 8A

```
# assign SNPs in clusters to patches in SNP.array in serpentine pattern
for (i in 1:len.clus) {
  cl <- clus[,i]
  len.cl <- length(cl)
  x3 <- c(x.cells[i]-1,x.cells[i],x.cells[i]+1)
  y3 <- c(y.cells[i]-1,y.cells[i],y.cells[i]+1)
  ndx <- round(sqrt(len.cl),0)
  p <- 1
  for (j in 1:ndx) {
    for (k in 1:ndx) {
      if (!is.na(cl[p])) SNP.array[x3[j],y3[k]] <- cl[p]
      p <- p + 1
      avail.patch.centers[i,i] <- 0
    }
  }
} randomize assignment of nonadjacent SNPs to patches in SNP.array
set.seed(1239)
x <- sample(length(x.cells), size=length(x.cells), replace=FALSE)
y <- sample(length(x.cells), size=length(x.cells), replace=FALSE)
nonadj.snp.seq <- sample(nonadj.snps, size=len.nonadj, replace=FALSE)
len.nonadj <- length(nonadj.snp.seq)
i <- 1
while (len.nonadj != 0) {
  for (j in 1:length(x.cells)) {
    if (avail.patch.centers[x[i],y[j]] != 0) {
      SNP.array[x.cells[x[i]],y.cells[y[j]]] <- nonadj.snp.seq[1]
      nonadj.snp.seq <- nonadj.snp.seq[-1]
      avail.patch.centers[x[i],y[j]] <- 0
      len.nonadj <- len.nonadj - 1
    }
  }
  i <- i + 1
} insure that array has no missing (NA) values in it
SNP.array[is.na(SNP.array[,])] <- 0
```

FIG. 8B.

```
###############################################################

#   Convolution of 2D array of genotype or other low-cardinality

######################################################### library(spatialfil)

genotypes at 30 SNPs
dat2 <- read.csv(file="c:/0_cerdsm/IP/VTE/Z.csv", header=TRUE,
         colClasses=rep("numeric",30))
len.Z <- length(dat2[[1]])
colnam <- colnames(dat2)
len.col <- length(colnam)
Z <- matrix(rep(0, len.Z*len.col), ncol=len.col)
for (i in 1:len.col) {
  Z[,i] <- dat2[[i]]
} inits
patch.nbr <- round(sqrt(len.col),0) + 1
patch.siz <- 5 # odd, so that each patch has a central cell surrounded on each side by 2 cells
SNP <- matrix(rep(0, (patch.nbr*patch.siz)^2), nrow=patch.nbr*patch.siz)
trainData <- matrix(rep(0, len.Z*patch.nbr^2), ncol=patch.nbr^2, byrow=TRUE)

# perform convolutions and summed intensities in each patch for each subject in training dataset
for (i in 1:len.Z) {
  for (j in 1:len.col) {
    # instantiate genotypes for each subject and apply Sobel and Gaussian convolutions in cascade
    loc <- match(j, SNP.array)
    x <- match(j,SNP.array)%%30
    y <- match(j,SNP.array[x,])
    if (Z[i,j] > 0) SNP[x,y] <- Z[i,j]
  }
  conv <- applyFilter(x=applyFilter(x=SNP, kernel=convKernel(k='sobel')),
            kernel=convKernel(sigma=1.4, k='gaussian'))
  patch.intensity <- rep(0, patch.nbr^2)
  m <- 1
  n <- 1
  for (k in 1:patch.nbr^2) {
    for (p in m:(m+4)) {
      for (q in n:(n+4)) {
        patch.intensity[k] <- patch.intensity[k] + conv[m,n]
      }
    }
    if (m < (patch.nbr - 1)*patch.siz) m <- m + 5
    if (n < (patch.nbr - 1)*patch.siz) n <- n + 5
    trainData[i,k] <- patch.intensity[k]
  }
}
```

FIG. 9.

```
################################################################

#   Deep learning model for VTE genomics with SKAT clustering and convolution of genotypes

########################################################## library(darch)

outcomes (VTE=1, no_VTE=0)
dat3 <- read.csv(file="c:/0_cerdsm/IP/VTE/y.csv", header=TRUE,
         colClasses="numeric")
len.y <- length(dat3[[1]])
colnam <- colnames(dat3)
trainTargets <- matrix(rep(0, len.y), nrow=len.y)
for (i in 1:len.y) {
  trainTargets[i] <- dat3[i,1]
} construct deep learning model
model2 <- darch(trainData, trainTargets, layers=c(2, 10, 1), darch.numEpochs=500, darch.stopClassErr=0,
retainData=T)

# determine model error rate
e <- darchTest(model2)
cat(paste0("Incorrect classifications on all examples: ", e[3], " (", e[2], "%)\n"))
# Incorrect classifications on all examples: 0 (0%)

# predict new case
predict(model2, SNP30)
# [1] 0.4370182        class=1
# use cutpoint of 0.35 for declaring VTE risk
```

FIG. 10.

CLASSIFIER APPARATUS WITH DECISION SUPPORT TOOL

INCORPORATION BY REFERENCE; DISCLAIMER

Each of the following applications are hereby incorporated by reference: application Ser. No. 16/595,073, filed on Oct. 7, 2019; application No. 62/742,362, filed Oct. 7, 2018. The applicant hereby rescinds any disclaimer of claims scope in the parent application(s) or the prosecution history thereof and advises the USPTO that the claims in the application may be broader than any claim in the parent application(s).

BACKGROUND

Classification is a machine learning technique. It arises frequently in bioinformatics applications, such as disease classifications using data like DNA sequences or DNA genotypes at particular SNP loci assayed with microarrays, and in artificial intelligence applications, such as automatic document classification and retrieval, text-mining sentiment analysis, and digital image recognition. Classification by machine learning may attempt to learn a mathematical function by analyzing training data consisting of sets of input features and a categorical (binomial or multinomial) output. The learned function then may be used to predict the class labels or statuses of new cases based on their input features. Examples of classification methods include (multiple) logistic regression, support vector machines, K-nearest-neighbor clustering methods, random forest, classification and regression trees, neural networks, Naive Bayes, and others.

There are circumstances including certain genomics applications, where these methods fail, are ineffective, or suffer from other limitations. For example, such circumstances include: when the number of training cases from which to learn is comparatively small; when the set of training cases is comprised of an admixture of two or more genotype or phenotype subgroups whose reasons and mechanisms for having their class label differ from the other subgroups; when the dimensionality of the input feature space is large; and when the rarity or unbalancing of some of the features' values is severe (partly on account of the subgroups admixture of which the overall group is comprised). In these circumstances, the conventional approaches to classification tend to be ineffective and yield high misclassification error rates.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies described herein may be utilized to provide an improved classifier apparatus and to improve accuracy of classification technology that may be employed as part of a decision support tool. In particular, an improvement may be realized by implementing a process including first applying a clustering to variables contributing to the classification task, the clustering may be determined according to a statistical relationship determined among the variables. For instance, the clusters may be represented in a 1-dimensional, 2-dimensional, or 3-dimensional matrix that is a spatial abstraction of the interrelationships. Next, one or more convolution transformations are applied to the matrix so as to reduce the effective dimensionality of the classification problem and improve the signal-to-noise ration. A deep learning (DL) neural network method may be applied to the transformed network to generate a DL classification model. Accordingly, subsequent new cases to be classified may be represented with variables placed in the same matrix arrangement, the same convolution transformation may be applied, and the DL model may be applied to determine the likely classification of the new cases.

At a high level, and according to an embodiment, from among a plurality of variables that may be potentially utilized by a classifier apparatus for determining a classification, statistical dependencies may be determined for these input variables. The input variables then may be assembled into an array comprised of clusters or variables, such as one-, two-, or three-dimensional arrays. In some embodiments, the numerical intensities of the cluster-members may be filtered so as to improve the signal-to-noise ratio for the purpose of pattern classification.

Next, a classification model may be established and trained based on characteristic patterns in the filtered arrays that correspond to two or more classes or states. Finally the classification model maybe utilized to classify a new set of input variables' values or to determine whether determined patterns manifest such features meriting decision-making or action. Some embodiments of the classifier apparatus may also adaptively provide statistically robust quantitative interpretations and electronic communication thereof.

BRIEF DESCRIPTION OF THE DRAWINGS

The present disclosure is described in detail below with reference to the attached drawing figures, wherein:

FIG. 2 depicts a flow diagram of a method for determining and utilizing an embodiment of the improved classifier apparatus for conditionally generating a notification regarding a patient's risk of a health condition called venous thromboembolism (VTE), based on phenotype information (such as the Padua Prediction Score) and based on genomics information, in accordance with an embodiment of the disclosure;

FIGS. 4A and 4B depict examples of strong and weak adjacency clustering, in accordance with an embodiment of the disclosure;

FIG. 6 depicts statistical performance of the example embodiment of the present disclosure actually reduced to practice and described in connection to FIG. 2; and FIGS. 7-10 illustratively provide an example embodiment of computer program routines for implementing a practical application of the improved classifier for VTE risk, described in connection to FIG. 2, and which determines composite-variables-of-composite-variables by digital filtering and deep learning.

DETAILED DESCRIPTION

Figure 1A:
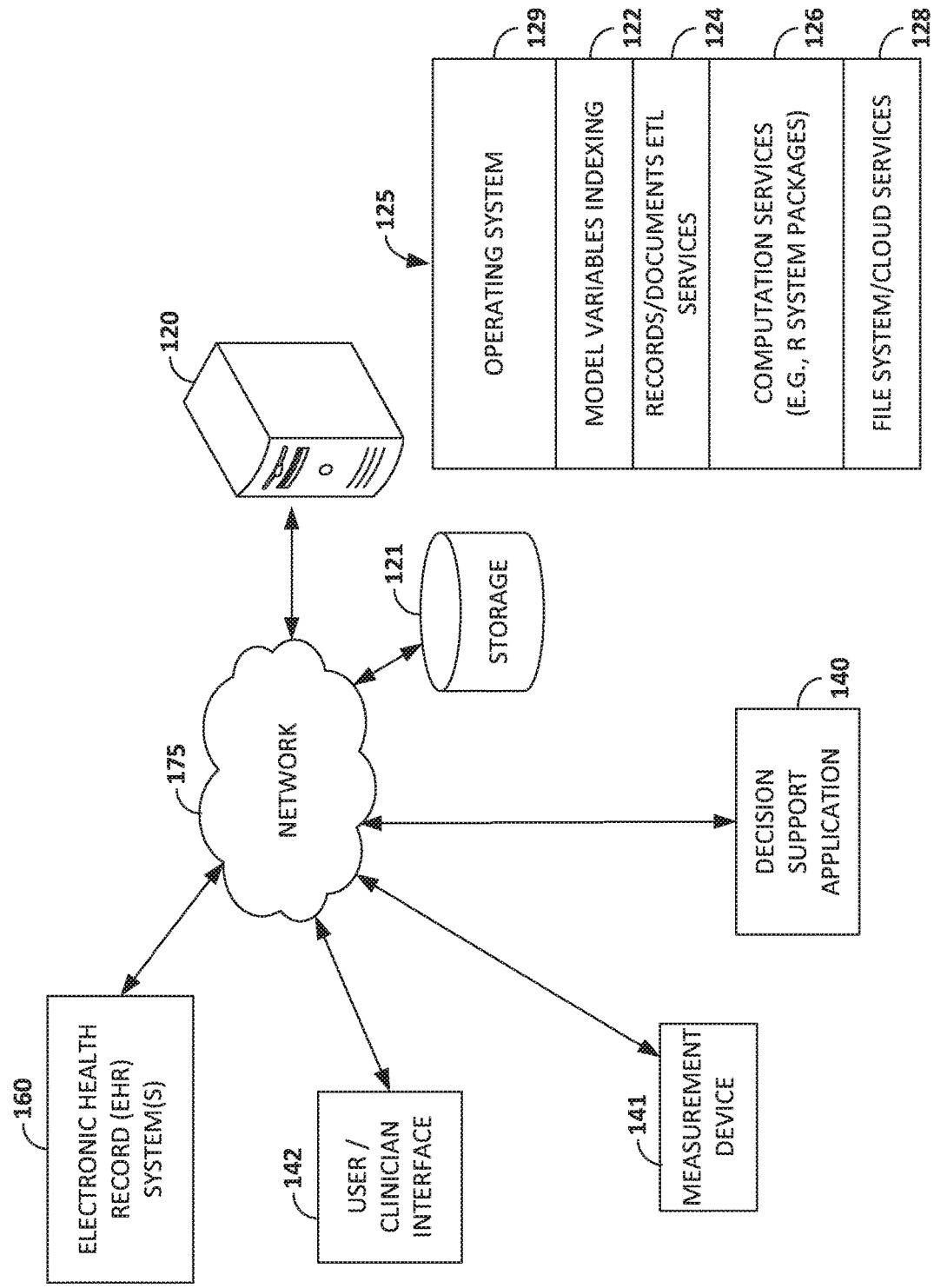
FIGS. 1A and 1B depict aspects of an illustrative operating environment suitable for practicing an embodiment of the disclosure.

The subject matter of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the technologies described herein may be embodied as, among other things: a method, system, or set of instructions embodied on one or more computer readable media, which is described herein. Accordingly, the embodiments may take the form of a hardware embodiment, a software embodiment, or an embodiment combining software and hardware. Some embodiments take the form of a computer-program product that includes computer-usable instructions embodied on one or more computer readable media.

At a high level, this disclosure describes, among other things, technologies for an improved classifier apparatus and processes for improving the accuracy of classification technology including example applications of such classifiers. Embodiments of these technologies may be utilized for preventive, diagnostic, and classificatory applications. Some embodiments also may be useful in a variety of industrial manufacturing and services processes that have high dimensionality and where identification of the status of the processes is desired. Additionally, some embodiments have applicability in bioinformatics and mammalian health diagnostics and prognostics having high dimensionality, unbalancing of the dependent (class label or status) variable, and where some input variables' values are missing or imprecisely known. For instance some example embodiments actually reduced to practice and described herein comprises a practical application of an improved deep learning classifier for determines a patient's risk for VTE, based on phenotype and genomics information.

Accordingly, an example embodiment is described for a decision support application for determining a patient's risk for VTE. In this example, a collection of controls and cases are acquired whose relevant collateral (phenotypic) covariables' values (X) are also known. For example, SNP genotype and phenotypic results are received. From the cases and controls, acquire additional values of a plurality of putatively causal variables (Z).

A "null model" may be determined. In some embodiments, the null model may be determined by logistic regression, multinomial regression, support vector machine, neural network, random forest, gradient boosting, or other suitable means, to establish the statistical relation of the covariables X to the endpoint classification y. For instance, one embodiment comprises calculating a phenotype only null model for endpoint association with phenotype. The resulting null model and metadata may be stored computer memory for subsequent use.

The association of genotypes with endpoint may be determined. In some embodiments, the null model may be used as an input to determine the statistical significance of relations of the plurality of variables Z to the endpoint classification y by a method, such as the Sequence Kernel Association Test (SKAT). Some embodiments may be carried out using the example computer program routine illustratively provided in FIG. 7, which may apply the SKAT method to determine VTE sequence kernel association.

Upon determining that statistically significant associations are present, network clustering may be performed to establish pairwise or multi-way correlations among the variables Z, thereby determining which variables (if any) are members of clusters and assigning the cluster members to locations adjacent or in proximity to each other in a one-, two-, or three-dimensional representation of the variables in a suitable 1-D, 2-D, or 3-D array. One embodiment comprises determining clusters and adjacency of alleles, such as intra- and inter-chromosome SNP genotype correlations-based adjacency. Some embodiments may be carried out using the example computer program routine illustratively provided in FIGS. 8A and 8B.

Figure 5:
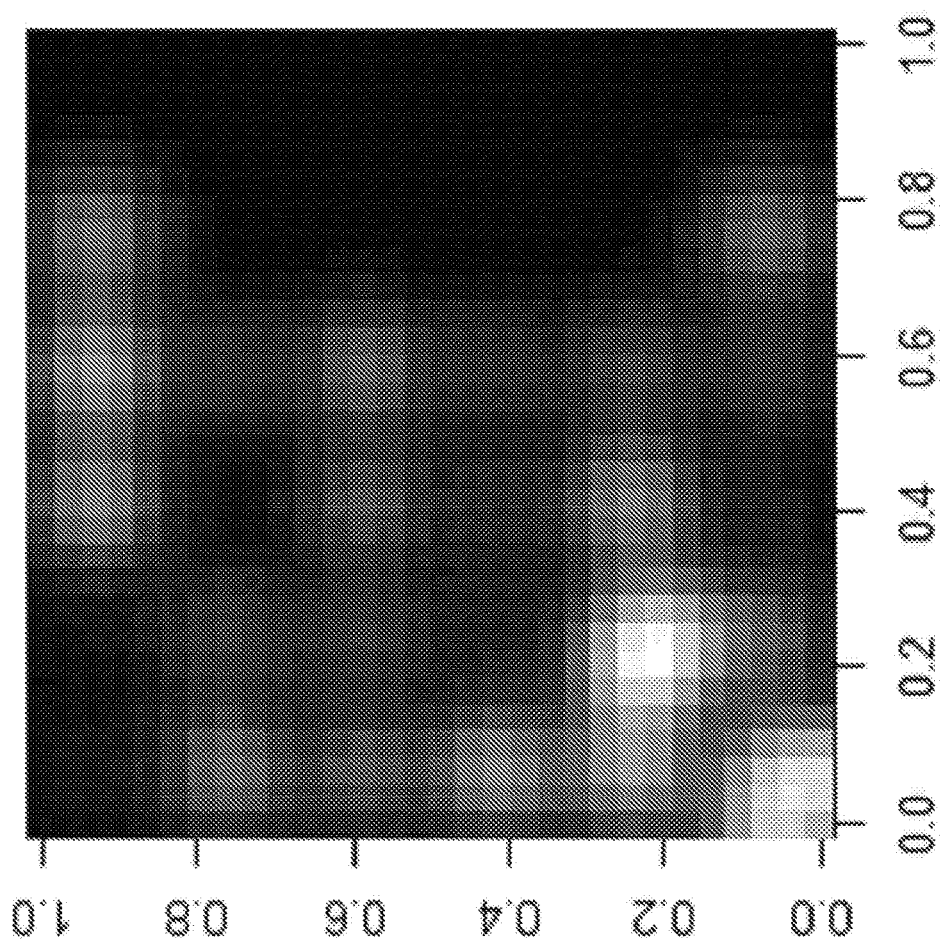
FIG. 5 depicts a graphical example of a Sobel-Gaussian Convolution Of Cluster Array, in accordance with an embodiment of the disclosure.

Variables that are not clustered members may be assigned to random positions in the array, such that none of these variables are in close proximity to another variable nor in close proximity to any cluster. Thus, the alleles may be reformatted with proximity of clustered alleles and random assignment of non-clustered members. Apply one or more convolution operations on the array, such as cascaded convolution with a Sobel filter and a Gaussian filter. An example illustrating Sobel-Gaussian convolution of a two-dimensional cluster array is depicted in FIG. 5. Some embodiments may be carried out using the example computer program routine illustratively provided in FIG. 9, which performs convolution on a two-dimensional array.

Optionally and in some embodiments, the numerical values (i.e., the "intensities") in disjoint subsets of the array (i.e., "patches") that correspond to regions to which cluster member variables and non-cluster member variables were assigned may be totalized. The array format, allele genotype mapping, and convolution-filtered array may be stored for subsequent use. A deep learning convolutional neural network may be applied to create a classification model, and store the deep learning classification model. The deep learning model may be applied to determine endpoint class and expectancy probability. Some embodiments may perform deep learning on the array with a kernel method, such as a convolutional neural network (CNN) to establish a classification model for the endpoint variable y as a function of covariates X and the clustered, convolution-transformed Z variables. Some embodiments for determining a classification model may be carried out using the example computer program routine illustratively provided in FIG. 10.

The expectancy probability may be evaluated against a threshold. The threshold may be pre-determined, determined by a clinician, or determined based on a condition of the patient. In an embodiment, a threshold of fifty percent is utilized. Where the threshold is not satisfied, then it may be determined that the patient does not have a sufficient risk for the condition. In an embodiment, a decision support tool may advise that results do not indicate a risk for VTE (or other condition using the improved classifier apparatus). In some embodiments, the classifier may be reapplied for the patient continuously, periodically, or as needed.

Where the threshold is satisfied, and thus the expectancy probability, which may correspond to the patient's risk for VTE, is high or at least above the threshold, then the decision support tool may advise that results are consistent with risk of endpoint class. In particular, a notification may be provided to a caregiver that the patient is at risk for VTE, and/or an intervening action may be invoked or otherwise carried out.

In some embodiments the statistical performance quality of the classification model may be determined. For example, in an embodiment, the statistical performance may be determined in terms of sensitivity, specificity, total error rate, or other criteria as are known in the art. The statistical performance of an embodiment actually reduced to practice is shown in FIG. 6. The determined model then may be implemented as a classifier apparatus such as part of a decision support apparatus. For example, new X and Z data may be acquired for one or more new cases whose likely endpoint value y is to be determined. The new cases' Z data may be transformed to the data array format, determined above, for cluster member and cluster-non-member variables. One or more convolution transforms may be applied to the new cases' arrays to obtain transformed arrays for these cases' Z data. Next the deep learning model determined above, may be applied to the X and transformed Z data. Based on the output, an advisory interpretive message may be electronically emitted regarding the model-generated classification.

As described above, embodiments of classifiers described herein improve upon conventional classification technologies. For instance, a problem occurring during a classification operation is that the dimensionality p of a feature vector is much larger than the available training sample size n. Further, in most cases, only a fraction of these p features are important in the classification operation. More specifically, one technical problem faced by conventional classifier applications is that the difficulty of high dimensional classification is intrinsically caused by the existence of many "noise features" that do not contribute to the reduction of classification error. One approach to feature selection in a high dimensional setting is to use two-sample t-tests to select important features in classification problems. However, when an admixture of multiple subgroups is present, such feature engineering methods cause more problems by giving excessive weight to prevalent subgroups and their features, and unduly penalize or dismiss less common subgroups and their corresponding features and patterns.

At a population level, these conventional classification technologies can at times exhibit good accuracy and calibration with new test datasets when the datasets recapitulate the prevalences of the subgroups in the training datasets. (The features retained in the completed, validated model reflect the feature patterns exhibited by the majority.) However, when these machine-learning classification models are utilized on new individual cases or on new very small groups, it is impossible to know which subgroup, if any, the new cases are members of. In particular, a model that is dominated by population-level prevalences may be very inaccurate when applied to low-prevalence subgroups whose feature patterns may be different from high-prevalence subgroups.

High dimensionality is generally considered to be a problem and a liability that hampers the discovery of broadly accurate applications of classification models by statistical analysis of observed multi-dimensional data. But the embodiments of the technologies provided by this disclosure solve this problem and improve classifier technology. In particular, for the specific implementations of these embodiments, the high dimensionality of features paradoxically becomes an asset, enabling the discovery of statistically significant clusters of features, which allow the data to be represented in an array that accords spatial adjacency to cluster members. This, in turn, enables the application of convolution operations to the array so as to smooth or average features that are in proximity to each other, and performing deep learning upon the smoothed array to constitute a novel means to retain coarsened, smoothed, "derived" or "composite" features whose member elements may have otherwise been discarded by the conventional classifier technologies. Retention of the convolution-filtered derived features in the classification model thereby enables subsequent accurate classification of individual new cases whose raw features are similarly represented in the array format and convolution-filtered prior to being classified by the model.

By way of analogy, an effect of the embodiments described herein is analogous to the perceptual and cognitive processes involved in averted gaze and peripheral vision in animals and humans, whereby newly looming objects that are not in clear visual focus are in a high percentage of cases correctly comprehended and classified on the basis of their large-scale derived patterns and overall shape (silhouette or outline, and luminance or density). Detailed direct examination of all the detailed raw features may be neither necessary nor effective for the rapid approximate classification purpose, given the very wide diversity of detailed raw features' values. Indeed, were it not for the comparatively high dimensionality of the raw scene data, the derived "composite" features of overall shape would be too indistinct to be useful for avoidance of danger, predators, or other classification targets. According to embodiments of this disclosure, the same may be true in a large class of deep learning problems requiring accurate recognition of quasi-composite features in high dimensional data more generally.

Conventional technologies for classifying and interpreting high-dimensionality arrays of data also have other limitations and problems that are overcome by embodiments of the improved classifier described herein. For example, (1) the measurement and analytics methods utilized by conventional classifiers for high-dimensionality presently depend on the existence of very large cohorts upon which to discover and train the classifier, under applicable multiple-testing (e.g., Bonferroni, FWER, and FDR) statistical methods. When the dimensionality of the classification problem to be solved is very high, or when a hierarchy of nonlinear inter-dependencies among the plurality of input variables is incompletely characterized, or when many of the input variables' values are unavailable or imprecisely measured, then impracticably large cohorts of subjects are required in order to statistically power analyses to determine a stable and accurate classification model.

Additionally, (2) the underlying statistical methods utilized to produce the classifications by conventional technology are ones that are readily defeated by the natural diversity of features encountered in real-world case material. The associated combinatorial explosion of patterns results in an underdetermined analytical problem, such that statistical sensitivity and specificity when the classifier is presented with new data are low, with many false-positive Type I errors and false-negative Type II errors.

Additionally, (3) in the case of genomics data, the conventional technology frequently lacks the means to minimize the impact of linkage disequilibrium (LD), to reduce the risk that the larger components may embody long stretches of LD rather than population structure, such that the long interrelated stretches encompassing a plurality of polymorphisms may be misconstrued as manifesting population structure, leading to high false-discovery rates and inaccurate classifications.

Additionally, (4) a priori unknown admixture of two or more phenotypic groups or genotypic pattern-based strata in the sampled population, particularly admixture of protective and risk rare variants, interferes with identification of groups (clusters), reduces statistical power, and increases the Type II false-negative error rate.

Additionally, (5) unbalancing of prevalences of cases and controls and/or unbalancing of values' statistical distributions of some independent variables (e.g., rare variants with low minor allele frequencies) results in reduction of statistical power for prior art association analyses and discovery of classification models.

Additionally, (6) the classification apparatus and methods utilized by conventional technologies are complex and do not emulate human learning and pattern-recognition processes in high-dimensionality situations. As a consequence, these apparatus and methods produce models that do not convey the "gist" or intuitive impression that expert human observers may form when presented with new data embodying patterns not previously encountered.

Additionally, (7), the conventional technology accords excessive evidentiary strength to the input variables that are from historical case material, can be statistically most strongly-associated with the classification outputs. As such, these conventional classifiers manifest model accuracy perishability, going further out of calibration with the passage of time, plus a resistance to taking newly-accruing information into account, particularly information involving input types that were not feasible to acquire during historical periods. The result is that the conventional-technology models' accuracy progressively deteriorates and fails to take advantage of newly-emerging statistical associations and inter-dependencies among input variables.

Additionally, (8) the conventional technology paradoxically accords excessive negative evidentiary strength to features that have low frequency. When the rare features are present they have strong causal influence or strong dependencies with other input variables, but in many cases some of those other variables' values may be missing or unmeasured. As such, the conventional classifier apparatuses manifest false-negative error rates, due to the preponderant absence of evidence that would be corroborating of the rare feature that is present.

Additionally, (9) the conventional technology is sensitive to imprecision in the measurements of input variables, such that classifications may be unstable when a given item is repeatedly measured and reclassified.

These and other deficiencies and limitations of the conventional technologies are mitigated or overcome by the improved technologies described herein. Many of these embodiments are also not susceptible to biases, that smooth or 'gist' the values of input variables that exhibit significant statistical relationships or dependencies with each other, and that take advantage of newly-emerging diagnostic technology or knowledge pertaining to input variables, such that very large cohort sizes are not required in order to reliably incorporate said technology or knowledge.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure other aspects of these technologies. Thus for readability, we show and reference items in the singular (while fully contemplating, where applicable, the plural).

As shown in FIG. 1A, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including a classifier apparatus, which may be incorporated into a decision support application. For example, in an embodiment, environment 100 may be used for monitoring, detecting or determining, and/or predicting a likely occurrence (or event) or future occurrence (or event) of VTE or another condition in a human patient, and additional decision support technology to facilitate caring for patients who may be prone to experience these conditions.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., a computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, and insurance, collections or claims records systems; and may be implemented in or as a part of computer system 120. Similarly, EHR system(s) 160 may perform functions for two or more of types of EHR systems (not shown). EHR system(s) 160 also may include records of physiological variables (such as vital signs measurements) obtained via one or more measurement apparatus, tests, or screenings, such as measurement device 141.

In some embodiments of the technologies described herein, aspects of a decision support tool for patients having or at risk for developing a condition or event occurrence, such as VTE, or recurrence of a condition or event may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, support-surface, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system(s) 160 directly. For example, in one embodiment a decision support application 140 operating at least in part on a client device (such as a user-operated computer device like a tablet) includes an interface 142 (which may comprise a graphical user interface), which may be used for accessing patient information from an EHR system(s) 160.

An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to have or develop a condition or health event, such as VTW, which may occur at a future time, and may further include a degree or level characterizing the severity of the condition or event. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; physiological variables or other patient-related measurements, time series, and predictions (including plotting or displaying the determined outcome and/or issuing an alert) described herein; or other health-related information, and facilitates the display of results, recommendations, or orders, for example. In an embodiment, application 140 also facilitates determining, receiving, or providing: notifications, recommendations, care plan changes, or orders, staffing scheduling, and/or queries from a user, which may be based on the results of monitoring and/or forecasted outputs, and which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical caregiver, physical therapist, or the like) to a probability, likelihood, forecast, score or prediction determined according to the technologies described herein, including information indicating a likelihood that a patient is experiencing a particular condition, such as VTE, or will experience such as condition or event, or other aspects described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined measurements, forecast(s), probabilities (or score), recommendations, scheduling orders, providing instructions (such as measuring, recording, and/or otherwise obtaining vital signs or other physiological variable measurements), confirmations or notifications (which may include, for example, confirmation that information has been received or notifications that information has not been received and there may be an error in the measuring instrument, user operation of a measurement device, or measurement procedure), reminders (such as notifications to obtain a physiological measurement sample), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for facilitating diagnostic services or evaluation of the performance of various embodiments.

Example operating environment 100 includes measurement device 141 communicatively coupled through network 175 to an EHR system 160. In an embodiment, measurement device 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, which may comprise input data into a classifier component of a decision support tool, and which may be acquired periodically, continuously, as needed, or as they become available, and may be represented as one or more time series of measured variables. In one embodiment, measurement device 141 comprises sensors for obtaining (and in some instances pre-processing or interpreting) non-invasive recording of vital signs, which may be obtained continuously, periodically, or at irregular intervals. Accordingly, the term measurement is used broadly herein, and it is contemplated that in some embodiments, measurement device 141 may not perform measurement but may receive information about physiological parameters (such as genotypic or phenotypic information, other measurements such as heart rate (HR), blood pressure (e.g., systolic blood pressure or SBP), respiratory rate (RR), for example and without limitation) which may be measured, observed, or otherwise recorded. Some embodiments of measurement device 141 may comprise one or more sensors, an interface component, and/or processing/communications component (not shown).

In some embodiments, measurement device 141 may include a Bluetooth or wireless communication data-transfer capability and may be wirelessly communicatively coupled with an application on a computing device, such as a smartphone an app or aspect of decision support application 140. In some embodiments, measurement device 141 comprises patient bedside monitor, such used in hospital. In an embodiment, one or more sensor components of measurement device 141 may comprise a user-wearable sensor component or sensor component integrated into the patient's environment. Examples of sensor components of measurement device 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the technologies disclosed herein may be received from human measurements, human observations, or automatically determined by sensors in proximity to the patient. For example, in one embodiment, a nurse periodically measures a patients' blood pressure and enters the measurement and/or observations via user/clinician interface 142. In another example, a nurse or caregiver enters one or more progress notes for an in-patient via user/clinician interface 142. Similarly, values for other physiological variables or patient data may be entered via user/clinician interface 142.

Examples of physiological variables monitored by measurement device 141 can include vital signs variables, such as heart rate (bradycardia and tachycardia) and blood pressure (hypotension and hypertension), oxygen saturation (peripheral desaturation), other vital signs, or physiologic or patient as described herein, such as genotypic or phenotypic information. In some embodiments physiological variables monitored by measurement device 141 may include any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making. In an embodiment, a measurement device 141 comprises a sensor probe and a communication link that periodically transmits identification information and probe data to a decision support application 140, so that a time series of monitored values is stored in a record associated with the patient on an EHR system 160, thereby enabling the decision support application 140 to form a raw binary alarm indication and/or a physiological variable decision statistic.

Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received) information from measurement device 141 to computer system 120. Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing (or mapping) service 122 and records/documents ETL service 124 provide services that facilitate retrieving patient variables such as physiological or other measurements, which may include frequent item sets, extracting database records, and/or cleaning the values of variables in records. For example, services 122 or 124 may perform functions for synonymic discovery, indexing or mapping variables in records, or mapping disparate health systems' ontologies, such as determining that a particular medication frequency of a first record system is the same as another record system. Some embodiments of stack 125 may also include predictive models service (not show), which in general is responsible for providing models such as multi-variable models, for detecting or predicting a particular condition or event utilizing a classifier apparatus, such as described herein. In some embodiments, services 122 and/or 124 may invoke computation services 126.

Computation services 126 may perform statistical software operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at cran.r-project.org) or similar services. In an embodiment, computation services 126 and include computer-performed services or routines, which may be embodied as one or more software agents or computer program routines such as the example embodiments of computer program routines illustratively provided in FIGS. 7-10. In one embodiment, computation services 126 comprises the R-System SKAT package, for performing kernel-regression-based association tests; the R-System netgwas package, for network-based genome-wide association calculations; the R-System spatialfil package, for performing filter operations on matrices or three-dimensional array data using convolution kernels; and the R-System darch package, for performing operations related to deep neural networks. Additional details about these example computation services 126 are included in the example computer program routines of FIGS. 7-10, and described further in connection to FIG. 2.

Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 7-10. Computation services 126 also may include services or routines for utilizing one or more classification models or processes, such as described in connection to FIG. 2 and the example computer program routines illustratively provided in FIGS. 7-10. In some embodiments, computation services 126 use EHR system(s) 160, model data and model storage services (not shown), and/or other components of example operating environment 100, and may also include services to facilitate receiving and/or pre-processing physiological (or other patient-related) data. For instance, model data and model storage services may be utilized to perform services for facilitating storage, retrieval, and implementation of the forecasting models described herein and of the data used in models, classifier apparatus, or predictive services.

In some embodiments, stack 125 includes file system or cloud-services 128. Some embodiments of component 128 may comprise an Apache Hadoop and Hbase framework, or similar frameworks operable for providing a distributed file system, and which in some embodiments facilitate provide access to cloud-based services, such as those provided by Cerner Healthe Intent®. Additionally or alternatively, some embodiments of file system or cloud-services 128 or embodiments of stack 125 may comprise one or more stream processing service(s). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient diagnoses or determinations, recommendations; recommendation knowledge base; recommendation rules; recommendations; recommendation update statistics; an operational data store, which stores events, frequent item sets (such as "X often happens with Y", for example), and item sets index information; association rule-bases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
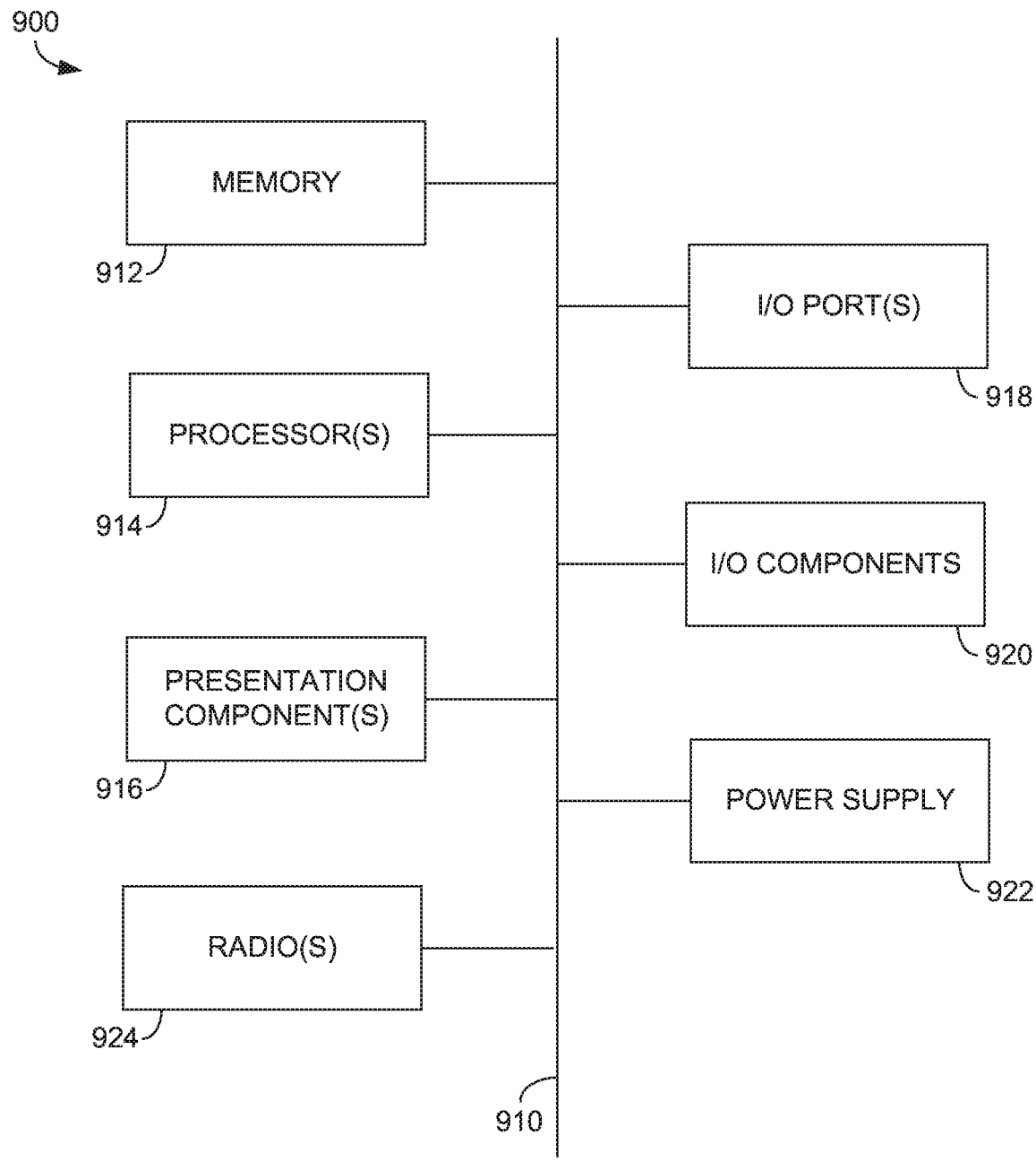

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. In an embodiment, storage 121 is embodied as memory 912. Presentation component(s) 916 present data indications to a user or other device. Exemplary presentation components include a display device, speaker, printing component, vibrating component, etc. In an embodiment, functionality provided via user/clinician interface 142 is facilitated by one or more presentation components 916.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Turning now to FIG. 2, one example embodiment of a method 200 for conditionally initiating an inventing action, which may include generating a notification, regarding a patient's risk of a health condition called venous thromboembolism (VTE), based on phenotype information (such as the Padua Prediction Score) and based on genomics information. In particular, method 200 generates and utilizes an embodiment of an improved classifier apparatus for determining the patient's risk of VTE.

Example method 200 includes step 202, wherein SNP genotype and phenotypic results are received. For example, receive a set of genotype and phenotypic physiological data about a patient. More generally, in some embodiments of step 202, a collection of controls and cases are acquired whose relevant collateral (phenotypic) covariables' values (X) are also known. Some embodiments of method 200 may further include, at step 204, associating a particular patient with the measurement device 141, and/or binding information about the patient or patient's EHR and initializing a data.frame (e.g., attributes and current date) for acquiring the phenotypic or genotypic data. In some embodiments, the operational data store (events) at step 207 may be received at step 204.

At step 206, receive SNP genotype and phenotypic results, plus endpoint status (if any). More generally, embodiments of step 206, acquire additional values of a plurality of putatively causal variables (Z), from the cases and controls. In some embodiments SNP genotype and phenotypic results may be received from operational data store (events) at step 207. At step 210, determine a "null model." In some embodiments, the null model may be determined by logistic regression or other suitable means, to establish the statistical relation of the covariables X to the endpoint classification y. For instance, in an embodiment, this step 210 comprises calculating a phenotype only null model for endpoint association with phenotype. The resulting null model and metadata may be stored computer memory for subsequent use.

At step 220, determine the association of genotypes with endpoint. In some embodiments of step 220, the null model may be used as an input to determine the statistical significance of relations of the plurality of variables Z to the endpoint classification y by a method, such as the Sequence Kernel Association Test (SKAT). Some embodiments of step 220, may be carried out using the example computer program routine illustratively provided in FIG. 7, which applies the SKAT method to determine VTE sequence kernel association. For example, at step 220, a null model may be determined for the endpoint classification in association with the genotype and phenotypic physiological data.

At step 230, upon determining that statistically significant associations are present, perform network clustering to establish pairwise or multi-way correlations among the variables Z, thereby determining which variables (if any) are members of clusters and as signing the cluster members to locations adjacent or in proximity to each other in a one-, two-, or three-dimensional representation of the variables in a suitable 1-D, 2-D, or 3-D array. In an embodiment, step 230 comprises determining clusters and adjacency of alleles, such as intra- and inter-chromosome SNP genotype correlations-based adjacency. Some embodiments of step 230, may be carried out using the example computer program routine illustratively provided in FIGS. 8A and 8B. For example, at step 230, an array of clusters of alleles may be determined based at least in part on the null model and the genotype and phenotypic physiological data based on the endpoint classification.

At step 240, assign variables that are not clustered members to random positions in the array, such that none of these variables are in close proximity to another variable nor in close proximity to any cluster. Thus, in step 240, the alleles may be reformatted with proximity of clustered alleles and random assignment of non-clustered members. At step 250, apply one or more convolution operations on the array, such as cascaded convolution with a Sobel filter and a Gaussian filter. An example illustrating Sobel-Gaussian convolution of a two-dimensional cluster array is depicted in FIG. 5. Some embodiments of step 250, may be carried out using the example computer program routine illustratively provided in FIG. 9, which performs convolution on a two-dimensional array. For example, at step 250, a classification model may be computed using a convolutional neural network and based at least in part on the array of clusters of alleles.

Next, in some embodiments, totalize the numerical values (i.e., the "intensities") in disjoint subsets of the array (i.e., "patches") that correspond to regions to which cluster member variables and non-cluster member variables were assigned. At step 245, the array format, allele genotype mapping, and convolution-filtered array may be stored for subsequent use. At step 260, apply deep learning convolutional neural network to create classification model, and store the deep learning classification model, in step 265. At step 270, apply deep learning model to determine endpoint class and expectancy probability. Some embodiments of step 260 and 270 may perform deep learning on the array with a kernel method, such as a convolutional neural network (CNN) to establish a classification model for the endpoint variable y as a function of covariates X and the clustered, convolution-transformed Z variables. For example, at step 270, an expectancy probability may be determined based on the classification model. Some embodiments for determining a classification model of step 260, may be carried out using the example computer program routine illustratively provided in FIG. 10.

At step 275, the expectancy probability may be evaluated against a threshold. The threshold may be pre-determined, determined by a clinician, or determined based on a condition of the patient. In an embodiment, a threshold of fifty percent is utilized. Where the threshold is not satisfied, then it may be determined that the patient does not have a sufficient risk for the condition. For example, at step 275 it may be determined that the patient is at risk for VTE when the threshold is satisfied, based on a comparison of the determined expectancy probability and a threshold. In an embodiment, at step 290, a decision support tool may advice that results do not indicate a risk for VTE (or other condition using the improved classifier apparatus). In some embodiments, the classifier may be reapplied for the patient as needed, and method 200 may return to step 202.

Where the threshold is satisfied, in step 275, and thus the expectancy probability, which may correspond to the patient's risk for VTE, is high or at least above the threshold, then at step 280 a decision support tool running method 200 may initiate an intervening action. For example, at step 280 an intervening action for a patient may be initiated. For instance, a notification may be provided to a caregiver that the patient is at risk for VTE, and/or another intervening action may be invoked or otherwise carried out. For instance, one intervening action comprises generating a notification that may be emitted or otherwise communicated to the patient or to a caregiver, such as a provider clinician responsible for the care of the patient. For example, an electronic advisory or warning message may be emitted to a human user, such as a caregiver, indicating an elevated risk of VTE for the patient. In an embodiment, the action comprises generating and emitting or communicating the notification, which may be emitted/communicated via a bedside or patient-side alarm, user/clinician interface (such as interface 142 described in FIG. 1A), or may be communicated to a smartphone or personal computing device of a caregiver, thereby alerting them of an impending deterioration of the patient's condition. In one embodiment, the notification comprises an event signal and includes the likelihood of future VTE.

Another intervening action that may be initiated, based on the determined likelihood, comprises modifying a care plan or treatment procedure or a recommendation for modifying a care plan or treatment procedure associated with the patient; for example, automatically scheduling an appointment with a specialist or other healthcare resources for the patient, operating on the patient, or administering another similarly effective therapeutic intervention. The recommendation may be provided in conjunction with a notification, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined likelihood of VTE occurrence. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, a physical therapy resource may be automatically reserved for the patient, healthcare staff may be notified and/or automatically scheduled, or transportation/support staff or resources for getting the patient to a healthcare facility may be called. In one embodiment, this action comprises modifying or updating a resource/scheduling electronic record in a resource/scheduling system, such as operated as part of a hospital or healthcare system. In some embodiments, the action comprises, upon a determined likelihood of a VTE event occurrence, initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

In some embodiments, the expectancy probability may be evaluated below the threshold at step 275. In these embodiments, at step 290, a caregiver may be alerted that evidence is thus far equivocal. For example, a display on a presentation component may be generated for the caregiver.

In some embodiments of method 200, the statistical performance quality of the classification model, determined in step 260, may be determined. For example in an embodiment, the statistical performance may be determined in terms of sensitivity, specificity, total error rate, or other criteria as are known in the art. The statistical performance of an embodiment actually reduced to practice is shown in FIG. 6. The determined model then may be implemented as classifier apparatus such as part of a decision support apparatus. For example, new X and Z data may be acquired for one or more new cases whose likely endpoint value y is to be determined. The new cases' Z data may be transformed to the data array format determined above, such as in steps 220 and 230 for cluster member and cluster-non-member variables. One or more convolution transforms then may be applied to the new cases' arrays to obtain transformed arrays for these cases' Z data. Next the deep learning model determined above, in step 260, may be applied to the X and transformed Z data. Based on the output, an advisory interpretive message may be electronically emitted regarding the model-generated classification.

Example Reduction to Practice

With reference to FIGS. 3, 4A-4B, 5, and 7-10, and with continuing reference to method 200 of FIG. 2 an example is provided of an embodiment of the disclosure constructively reduced to practice. In this example, a decision support tool comprising an embodiment of the improved classifier apparatus was utilized to determine patients at risk for VTE, based on phenotype information (such as the Padua Prediction Score) and based on genomics information.

The records of one thousand persons experiencing venous thromboembolic events (VTE, as determined by clinical exam) during medical or surgical admissions to 451 U.S. acute-care hospitals between 01-JAN-2010 and 31-DEC-2016 were retrieved and screened, as were the records of 1,000 age-gender-medical service matched persons admitted to the same institutions during the same time period who did not experience VTE. These records were retrieved from Cerner Health Facts® data warehouse, an electronic health record (EHR 160) derived, HIPAA-compliant de-identified repository containing the longitudinally-linked health records of more than 100 million persons receiving care at 824 U.S. based institutions. Informed consent was obtained from candidate subjects screened and invited to participate in the study, for genomics testing of 30 single nucleotide polymorphisms (SNPs) that are known from the research literature to be associated with risk of developing VTE.

Figure 3:
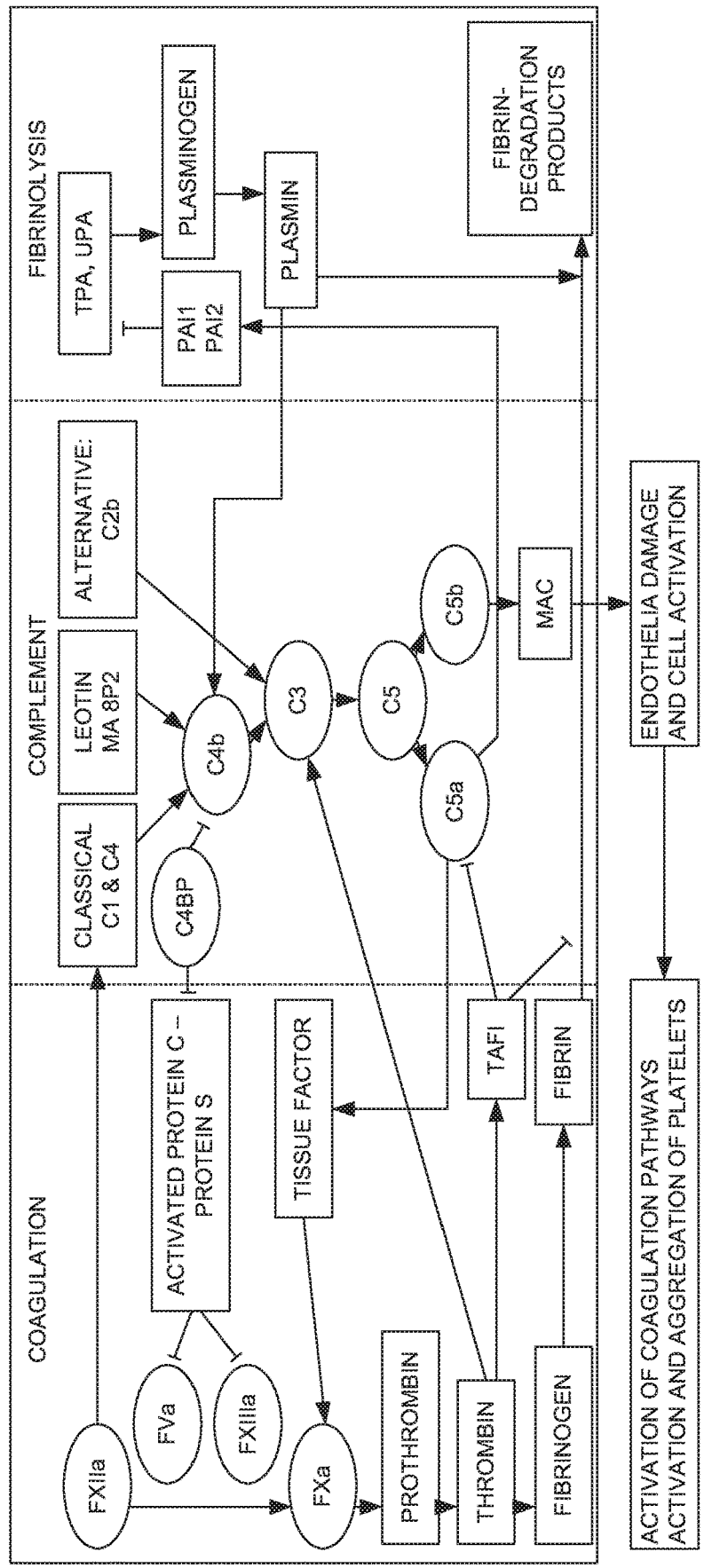
FIG. 3 depicts a flow chart characterizing the biochemistry of coagulation, with regards to the example embodiment described in connection to FIG. 2.
Figure 4B:
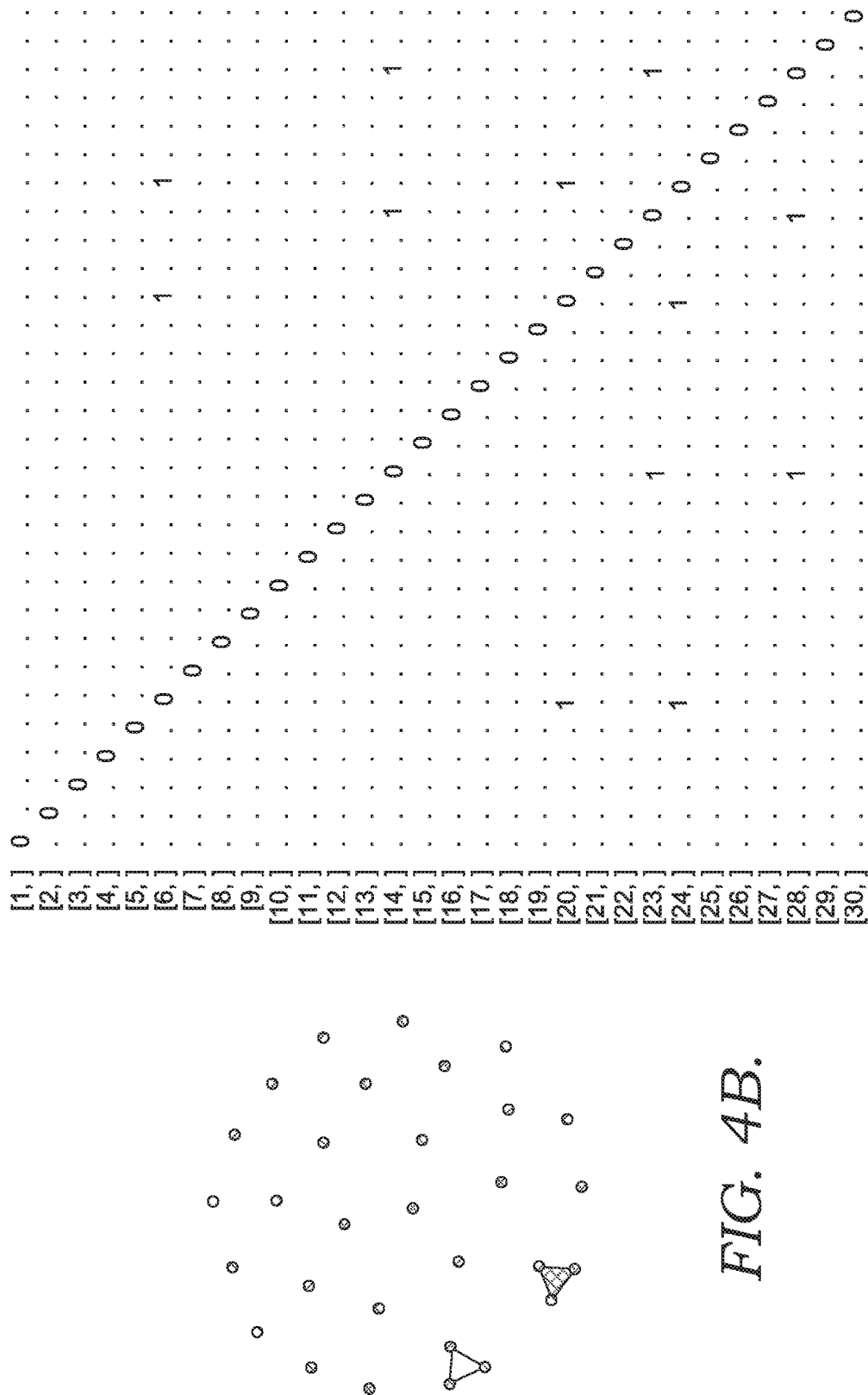

Venous thrombosis and venous thromboembolism (VTE), usually evolving from thrombophilia and commonly manifested as deep venous thrombosis (DVT) and pulmonary embolism (PE), are a major health concern worldwide. There are many phenotypic and demographic risk factors, but there are also many known strong genetic risk factors for VTE. These involve deficiencies in the innate anticoagulants protein C, protein S and anti-thrombin. These genetic variants typically occur with low frequencies (<1%) in the general population due to their severity. With reference to FIG. 3, uncommon functional impairments due to genetic variations in the pro-coagulants such as fibrinogen, prothrombin (factor II), factor V, Factor XI, and Factor XII are also associated with VTE. The two most evaluated genetic risk factors for VTE are factor V Leiden (rs6025; causing protein C resistance and a hypercoagulable, prothrombotic phenotype) and prothrombin G20210A (rs1799963), each of which increases thrombotic risk by threefold to fivefold and, jointly, up to 20-fold. By contrast, non-O blood groups are also a known risk factor for VTE, and such blood group genetic variations have high prevalence in the general population. Widely disparate prevalences such as these ordinarily interfere with determining broadly accurate classification models.

Genotypes for the DNA SNP locations were determined from enrolled subjects' saliva specimens by testing using the Illumina HumanOmniExpress-24® microarray chip and associated Illumina assay reagents and instrumentation (measurement device 141). Only cases and controls having complete genotypes (no missing values or "no-calls") for the 30 SNPs were included for analysis (as the Z data). The Padua Predictive Score for VTE risk was obtained for each patient during the first 24 hours of each patient's admission to hospital and utilized as a phenotypic biomarker denoting propensity for incident VTE. The Padua Score was dichotomized at a cut point value of 3 (values less than or equal to 3 coded as 0; values greater than 3 coded as 1) as the X covariable in subsequent analysis.

The following 30 alleles (SNP polymorphisms) at loci in 24 genes on 11 chromosomes were genotyped and utilized in this actual reduction-to-practice: ABO (rs514659, rs8176719, rs2519093, rs495828), ADAMTS13 (rs4075970, rs142572218, rs121908473), antithrombin SERPINC1 (rs786204063), B3GAT2 (rs1304029, rs2748331), BLZF1 (rs7538157), F2 G20210A variant (rs1799963), F5 Leiden (rs6025), Flt (rs4241824), F12 (rs1801020), FGG (rs2066865), GP6 (rs1613662), IL-6 G572C variant (rs1800796), KNG1 (rs710446), NME7 (rs16861990), P2RY12 T744C variant (rs2046934), protein C PROC (rs1799810), protein C receptor PROCR (rs867186), protein S PROS1 (rs138925964), RIMS1 (rs41265501), SLC19A2 (rs2038024), SLC44A2 (rs2288904), SMAP1 (rs11243995), THSD7A (rs2074597), and TNF G308A variant (rs1800629). As used throughout this document, "rs" may be values from the national institute of health "genblock" sequence database, as someone of ordinary skill in the art may access. In population genetics, linkage disequilibrium is, by definition, the non-random association of alleles at different loci in a given population. Loci are said to be in linkage disequilibrium when the frequency of association of their different alleles is higher or lower than what would be expected if the loci were statistically independent. The mechanisms that give rise to linkage disequilibrium are many. However, loci that are on different chromosomes or that are far apart on the same chromosome are less likely to be jointly inherited so as to exhibit linkage disequilibrium. By contrast, loci that are in proximity to each other on the same chromosome ("adjacency") are likely to be found to be statistically associated (dependent) and in linkage disequilibrium. Among the 30 SNP alleles analyzed in this illustrative example, linkage disequilibrium was exhibited by 12 of the alleles.

In this example embodiment actually reduced to practice, computer system 120 running the Linux operating system (129) was utilized with the open-source software package R, and the R packages (computation services 126): SKAT, for performing a sequence kernel association test of the statistical significance of the $\{Z_j\}$ genomics features adjusting for the null model with $\{X_i\}$ features; package netgwas for determining clusters of the $\{Z_j\}$ genomics features; package spatialfil for performing Sobel and Gaussian convolutions; and package darch for generating a deep learning DL classification model on the convolution-filtered array of clustered $\{Z_j\}$ genomics features with respect to the VTE outcome class $\{y_k\}$. This example embodiment also used the example computer program routine provided in FIGS. 7-10.

The null model with Padua Prediction Score demographic and phenotypic features only had an accuracy of only 61%, with sensitivity 50% and specificity 72%. In contrast, the DL model based on the convolution-filtered clustered $\{Z_j\}$ genomics features had accuracy of 97%, with sensitivity 99% and specificity 95%, as depicted in FIG. 6, and thus represents a significant improvement over the conventional classifier technologies. In particular, embodiments of the example decision support tool for determining risk of VTE utilizing the improved classifier described herein may result in the saving of many additional patient lives.

Many different arrangements of the various components depicted, as well as components not shown, are possible without departing from the spirit and scope of the present disclosure. Embodiments of the technology provided in this disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present technologies. For example, although certain aspects of these technologies largely have been described with reference to the embodiment for detecting risk of VTE, embodiments of the improved classifier apparatus have significant versatility, and can be applied to a wide range of applications involving relational data. Examples include, but are not limited to applications involving: (1) sentiment classification in a text-mining system; (2) community identification in social network analysis; (3) clustering trading in financial instruments, particularly equities that are members in an index or are held by exchange-traded funds or other portfolios; and (4) interpreting genomics patterns in bioinformatics applications.

It will be understood that certain features and subcombinations are of utility and may be employed without reference to other features and subcombinations and are contemplated within the scope of the claims. Not all steps listed in the various figures need be carried out in the specific order described. Accordingly, the scope of the embodiments of the technologies described herein is intended to be limited only by the following claims.

As used herein and in connection with the clauses listed hereinafter, the terminology "any of clauses" or similar variations of said terminology is intended to be interpreted such that features of claims/clauses may be combined in any combination. For example, an exemplary clause 4 may indicate the method/apparatus of any of clauses 1 through 3, which is intended to be interpreted such that features of clause 1 and clause 4 may be combined, elements of clause 2 and clause 4 may be combined, elements of clause 3 and 4 may be combined, elements of clauses 1, 2, and 4 may be combined, elements of clauses 2, 3, and 4 may be combined, elements of clauses 1, 2, 3, and 4 may be combined, and/or other variations. Further, the terminology "any of clauses" or similar variations of said terminology is intended to include "any one of clauses" or other variations of such terminology, as indicated by some of the examples provided above.

Clause 1. A computer system for treating venous thrombosis and venous thromboembolism (VTE) in a human patient: a processor; computer memory having instructions stored thereon that when executed by the processor perform operations comprising: receiving a set of SNP genotype and phenotypic physiological data about the patient; determine a null model for end-point association with phenotype; determine association of genotypes with endpoint; determine clusters of adjacency of alleles to reformat the alleles as an array; perform convolution operations on the array; apply a convolutional neural network on the array to create an improved classification model; utilize the improved classification model to determine endpoint class and expectancy probability; based on a comparison of the determined expectancy probability and a threshold, determine that the patient is at risk for VTE when the threshold is satisfied; and initiate an intervening action for the human patient.

Clause 2. The system of clause 1 wherein the threshold is pre-determined, determined based on a parameter set by a clinician, a determined based on a condition of the patient.

Clause 3. The system of clause 1 wherein the intervening action comprises at least one of: issuing a notification to a caregiver associated with the patient; automatically scheduling healthcare resources for treating the patient; or modifying a computer program associated with a care plan for the patient.

Clause 4. A method for performing classification on a computer, comprising: receiving a data set having a plurality of types of data objects which are interrelated to each other, the data objects having attributes of respective data objects between predictor objects of the same type $\{Z_i\}$, and heterogeneous relations between objects of two or more different types, including predictor-variable objects $\{X_j\}$ and outcome or class-identifier objects $\{y_k\}$; determining a null classification model for $\{y_k\}$ as a function of $\{X_j\}$; using the null model to adjust for the influence of heterogeneous or phenotypic objects $\{X_j\}$, determining whether statistically significant relationship(s) exist associating $\{Z_i\}$ to $\{y_k\}$; determining a clustering of $\{Z_i\}$ as a network 1-D, 2-D or 3-D spatial abstraction representing mutual statistical relationships among the $\{Z_i\}$; rendering the spatial relationships of the network in a 1-D, 2-D or 3-D array; applying a convolution operation to the array to smooth and denoise the array's cells' values; formulating a classification model representing data objects and respective relationships of $\{X_j\}$ and $\{Z_i\}$ data objects to the $\{y_k\}$, the model comprising an expectation of object states $\{y_k\}$ generated based on a binomial or multinomial distribution; storing the classification model in computer memory; and utilizing the classification model within a classifier for a decision support application.

Clause 5. The method of clause 4 further comprising: receiving new data sets whose $\{X_j\}$ and $\{Z_i\}$ data objects are recast in the same array arrangement; performing convolution operation on the received new data sets; applying the classification model to in a decision support application to determine a condition of a patient; and based on the determined condition of the patient, initiating an intervening action when the patient is determined to have the condition.

Clause 6. The method of clause 5 wherein the classification model determines a resulting state vector $\{y_k\}$, and the resulting state vector $\{y_k\}$ is stored in the computer memory, and electronically communicated to a human user.

Clause 7. The method of clause 4, wherein the data set received comprises a collection of phenotype $\{X_j\}$ and genotype information $\{Z_i\}$ pertaining to a human subject, and the state vector $\{y_k\}$ comprises binomial or multinomial outcomes or classification indicia of a health condition.

Clause 8. The method of clause 4, wherein the null model is determined to establish the statistical relation of the covariables $\{X_j\}$ to the endpoint classifications $\{y_k\}$, and wherein the null model is determined by logistic regression, multinomial regression, support vector machine, neural network, random forest, or gradient boosting.

Clause 9. The method of clause 8, wherein the null model is used as an input to the classification model determine the statistical significance of relations of the plurality of variables $\{Z_i\}$ to the endpoint classification $\{y_k\}$.

Clause 10. The method of clause 9, wherein the Sequence Kernel Association Test (SKAT) is utilized to determine the statistical significant of relations.

Clause 11. The method of clause 4, wherein when statistically significant associations are identified, network clustering is performed to establish pairwise and multi-way correlations among the variables $\{Z_i\}$, and the processor partitions a graph according to the strength of said correlations.

Clause 12. The method of clause 4, wherein the correlations further determine a clustering of data objects $\{Z_i\}$ and determine which variables (if any) are members of clusters, and wherein the cluster members are assigned to locations adjacent or in proximity to each other in a 1-D, 2-D or 3-D representation of the variables in a 1-D, 2-D or 3-D array.

Clause 13. The method of clause 12, wherein variables in $\{Z_i\}$ that are not cluster members to random positions in the array, such that none of these variables is in close proximity to another variable nor in close proximity to any cluster.

Clause 14. The method of clause 4, wherein one or more convolution operations are applied to the array.

Clause 15. The method of clause 14, wherein the one or more convolutions comprise cascaded convolution with a Sobel filter and a Gaussian filter.

Clause 16. The method of clause 15, wherein at least one additional mathematical transformation is applied to the array, the at least one additional transformation comprising: setting to zero all array cells whose values are less than a "floor" value, or setting to a "ceiling" value all array cells whose values exceed a threshold value.

Clause 17. The method of clause 4, further comprising: determining the numerical values ("intensities") in disjoint subsets of the array that correspond to regions to which cluster member variables and non-cluster member variables were assigned; and totalizing the intensities.

Clause 18. The method of clause 4, wherein deep learning is performed on the array using a kernel method, to establish a classification model for the endpoint variables $\{y_k\}$ as a function of covariates $\{X_j\}$ and the clustered, convolution-transformed $\{Z_i\}$ variables.

Clause 19. The method of clause 4, wherein the kernel method comprises a convolutional neural network.

Clause 20. The method of clause 4, wherein determine the statistical performance quality of the classification model in terms of sensitivity, specificity, or total error rate.

Clause 21. The method of clause 4, wherein $\{X_j\}$ and $\{Z_i\}$ object data are acquired for one or more new cases whose likely endpoint value set $\{y_k\}$ is to be determined.

Clause 22. The method of clause 21, wherein the new cases' $\{Z_i\}$ objects' data are transformed to the array format for cluster member and cluster-non-member variables.

Clause 23. The method of clause 22, wherein the at least one convolution is applied to transform to the new cases' arrays thereby obtaining transformed arrays for the cases' $\{Z_i\}$ data.

Clause 24. The method of clause 23, wherein the weighting of the binomial or multinomial association model for y on $Z_i$ is defined by a logistic distribution ($w_i = \exp(a_1 - MA_i) a_2 / (1 + \exp(a_1 - MAF_i) a_2)$) or a beta distribution ($w_i = \text{beta}(MAF_i, a, a_2)^2$).

Clause 25. The method of clause 23, wherein the DL model is applied to the $\{X_j\}$ and transformed $\{Z_i\}$ data to yield a classification.

Clause 26. The method of clause 4, wherein an advisory interpretive message regarding the model-generated classification is electronically emitted to the user.

What is claimed is:

1. A system having a measurement device configured to acquire patient measurement data via a sensor and having one or more hardware processors configured to facilitate a plurality of operations for diagnosing and treating a venous thromboembolism (VTE) condition associated with a patient, the operations comprising:
    receiving, via the one or more hardware processors, a set of genotype and phenotypic physiological data associated with the patient;
    generating a null model for an endpoint classification in association with the genotype and phenotypic physiological data;
    determining, based at least in part on the null model and the genotype and phenotypic physiological data, an array of clusters of alleles based on the endpoint classification;
    determining, via the one or more hardware processors and based at least in part on training and utilizing a convolutional neural network and based at least in part on the array of clusters of alleles, a classification model;
    based on the classification model, determining an expectancy probability for the VTE condition;
    determining that the expectancy probability for the VTE condition meets a threshold; and
    increasing a frequency at which one or both of the measurement device and the sensor acquires measurements.

2. The system of claim 1, further comprising: determining, based on the null model, an association of a genotype with the endpoint classification; and, wherein determining the array of clusters of alleles, is further based at least on the association of genotype with the endpoint classification.

3. The system of claim 1, further comprising determining non-clusters of alleles, based at least in part on the genotype and phenotypic physiological data, and randomly assigning the non-clusters of alleles to the array of clusters of alleles.

4. The system of claim 1, wherein the threshold comprises a pre-determined expectancy probability, a determined expectancy probability based on a parameter set by a clinician, or a determined expectancy probability based on a condition of the patient.

5. The system of claim 1, wherein the intervening action is associated with at least one operation selected from a group of: issuing a notification to a caregiver associated with the patient; automatically scheduling healthcare resources for treating the patient; or modifying a computer program associated with a care plan for the patient.

6. The system of claim 1, wherein the measurement device is configured to obtain physiological measurements of from the patient, and wherein the operations further comprise obtaining the physiological measurements of from the patient based on the increased frequency.

7. The system of claim 1, further having a patient monitor configured to measure physiological changes in the patient, wherein the operations further comprise increasing a sensitivity of the patient monitor in response to determining that the patient is at risk for VTE and measuring the physiological changes in the patient based on the increased sensitivity.

8. A computer-implemented method for diagnosing and treating a venous thromboembolism (VTE) condition associated with a patient, comprising:
    receiving, via one or more hardware processors associated with a measurement device configured to acquire patient measurement data via a sensor, genotypic and phenotypic physiological data associated with the patient;
    determining a null model for an endpoint classification in association with genotypic and phenotypic physiological data;
    determining statistically significant relationships between the genotypic and phenotypic physiological data based on the null model;
    determining an array of clusters of alleles as a spatial abstraction representing the statistically significant relationships;
    determining, via the one or more hardware processors and based at least in part on training and using a convolutional neural network and based at least in part on the array of clusters of alleles, a classification model;
    based on the classification model, determining an expectancy probability for the VTE condition;
    determining that the expectancy probability for the VTE condition meets a threshold; and
    increasing a frequency at which one or both of the measurement device and the sensor acquires measurements.

9. The computer-implemented method of claim 8, further comprising:
    applying the classification model to determine a condition of a particular patient; and
    based on the condition of the particular patient, initiating an intervening action.

10. The computer-implemented method of claim 9, wherein the condition comprises a risk for VTE.

11. The computer-implemented method of claim 8, wherein the null model is determined by logistic regression, multinomial regression, support vector machine, neural network, random forest, or gradient boosting.

12. The computer-implemented method of claim 8, wherein a Sequence Kernel Association Test (SKAT) is utilized to determine the statistically significant relationships.

13. The computer-implemented method of claim 8, wherein the spatial abstraction is a 1-D, 2-D, or 3-D spatial abstraction.

14. The computer-implemented method of claim 8, further comprising determining that the array of clusters of alleles contains a cell with a value less than a floor value, and transforming the cell to zero.

15. One or more non-transitory media having computer-readable instructions that, when executed by one or more hardware processors associated with a measurement device configured to acquire patient measurement data via a sensor, cause the one or more hardware processors to facilitate a plurality of operations for diagnosing and treating a venous thromboembolism (VTE) condition associated with a patient, the operations comprising:
- receiving, via the one or more hardware processors, a set of genotype and phenotypic physiological data associated with the patient;
- generating a null model for an endpoint classification in association with the genotype and phenotypic physiological data;
- determining, based at least in part on the null model and the genotype and phenotypic physiological data, an array of clusters of alleles based on the endpoint classification;
- determining, via the one or more hardware processors and based at least in part on training and utilizing a convolutional neural network and based at least in part on the array of clusters of alleles, a classification model;
- based on the classification model, determining an expectancy probability for the VTE condition;
- determining that the expectancy probability for the VTE condition meets a threshold; and
- increasing a frequency at which one or both of the measurement device and the sensor acquires measurements.

16. The one or more non-transitory media of claim 15, wherein determining the array comprises building the array as a spatial abstraction representing the association of the genotype with the endpoint classification.

17. The one or more non-transitory media of claim 15, wherein the association of the genotype with the endpoint classification comprises a statistically significant relationship between the genotype and phenotypic physiological data based on the null model.

18. The one or more non-transitory media of claim 15, further wherein the threshold is a pre-determined expectancy probability, determined expectancy probability based on a parameter set by a clinician, or determined expectancy probability based on a condition of the patient.

19. The one or more non-transitory media of claim 15, further comprising binding the genotype and phenotypic physiological data to the patient.

20. The one or more non-transitory media of claim 15, wherein the expectancy probability comprises a probability of risk for VTE based on the set of genotype and phenotypic physiological data.

21. The one or more non-transitory media of claim 15, wherein the classification model is generated for display on a presentation component of a computing device associated with the one or more hardware processors.

22. The one or more non-transitory media of claim 21, wherein the intervening action comprises issuing a notification to a caregiver associated with the patient on the presentation component of the computing device.

23. The one or more non-transitory media of claim 15, wherein execution of the computer-readable instructions causes the one or more hardware processors to determine clusters and adjacency of alleles, and wherein the adjacency includes intra-or inter-chromosome SNP genotype correlations-based adjacency.

* * * * *